(12) United States Patent
Warr et al.

(10) Patent No.: US 8,580,728 B2
(45) Date of Patent: Nov. 12, 2013

(54) USE OF FRAGRANCE COMPOSITIONS FOR THE PREVENTION OF THE DEVELOPMENT OF INDOLE BASE MALODOURS FROM FECAL AND URINE BASED SOILS

(75) Inventors: Jonathan Frank Warr, Paris (FR); Maud Bernadette Bassereau, La Garenne Colombes (FR); Emmanuel Julien Aussant, Paris (FR); Stuart Bernard Fraser, Little Neston (GB)

(73) Assignee: Takasago International Corporation, Tokyo (JP)

( * ) Notice: Subject to any disclaimer, the term of this patent is extended or adjusted under 35 U.S.C. 154(b) by 572 days.

(21) Appl. No.: 12/639,715

(22) Filed: Dec. 16, 2009

(65) Prior Publication Data

US 2010/0104525 A1   Apr. 29, 2010

Related U.S. Application Data

(63) Continuation of application No. 11/499,226, filed on Aug. 4, 2006, now abandoned.

(51) Int. Cl.
| | |
|---|---|
| *A61K 8/00* | (2006.01) |
| *A61K 8/18* | (2006.01) |
| *A61Q 13/00* | (2006.01) |
| *A61L 9/00* | (2006.01) |
| *A61L 9/01* | (2006.01) |
| *B01D 53/34* | (2006.01) |
| *A61L 9/04* | (2006.01) |
| *A61L 11/00* | (2006.01) |
| *A62B 7/08* | (2006.01) |

(52) U.S. Cl.
USPC ............... 512/1; 512/25; 424/76.1; 424/76.2; 424/76.21; 424/76.4; 424/76.5; 424/76.6; 422/4; 422/5; 422/120

(58) Field of Classification Search
USPC ............. 422/4, 5, 120; 424/76.1, 76.2, 76.21, 424/76.4, 76.5, 76.6; 512/1, 25
See application file for complete search history.

(56) References Cited

U.S. PATENT DOCUMENTS

| | | | |
|---|---|---|---|
| 3,675,625 A | 7/1972 | Miller et al. | |
| 3,789,797 A | 2/1974 | Brewer | |
| 4,134,838 A | 1/1979 | Hooper et al. | |
| 4,278,658 A | 7/1981 | Hooper et al. | |
| 4,304,679 A | 12/1981 | Hooper et al. | |
| 4,322,308 A | 3/1982 | Hooper et al. | |
| 4,335,722 A | 6/1982 | Jackson | |
| 4,437,429 A | 3/1984 | Goldstein et al. | |
| 4,719,105 A | 1/1988 | Schleppnik | |
| 4,846,823 A | 7/1989 | Enloe | |
| 4,874,536 A | 10/1989 | Strickland, Jr. et al. | |
| 4,906,454 A | 3/1990 | Melanson, Jr. et al. | |
| 5,395,555 A | 3/1995 | Colurciello et al. | |
| 5,589,164 A | 12/1996 | Cox et al. | |
| 5,676,163 A | 10/1997 | Behan et al. | |
| 5,733,272 A * | 3/1998 | Brunner et al. ............... | 604/359 |
| 5,795,566 A | 8/1998 | Joulain et al. | |
| 5,932,495 A | 8/1999 | Boney et al. | |
| 5,942,217 A | 8/1999 | Woo et al. | |
| 5,955,093 A | 9/1999 | Woo et al. | |
| 6,031,147 A | 2/2000 | Gross | |
| 6,033,679 A | 3/2000 | Woo et al. | |
| 6,177,070 B1 | 1/2001 | Lynch | |
| 6,183,731 B1 | 2/2001 | Carey et al. | |
| 6,917,754 B2 | 7/2005 | Pedrotti et al. | |
| 2002/0010447 A1 | 1/2002 | Williams et al. | |
| 2003/0017960 A1* | 1/2003 | Bertrem et al. ............... | 510/475 |
| 2003/0044309 A1 | 3/2003 | Hernandez et al. | |
| 2003/0068295 A1* | 4/2003 | Rohde et al. ................. | 424/76.1 |
| 2004/0147416 A1 | 7/2004 | Woo et al. | |
| 2005/0124512 A1 | 6/2005 | Woo et al. | |
| 2005/0187123 A1 | 8/2005 | Li et al. | |
| 2005/0187124 A1 | 8/2005 | Li et al. | |

FOREIGN PATENT DOCUMENTS

| | | | |
|---|---|---|---|
| DE | 43 43 265 A1 | 6/1995 | |
| EP | 0 462 643 A1 | 12/1991 | |
| EP | 0 775 741 A1 | 5/1997 | |
| EP | 0 780 132 A1 | 6/1997 | |
| EP | 1 070 507 A1 | 1/2001 | |
| EP | 1 214 879 A2 | 6/2002 | |
| EP | 1469132 A2 | 10/2004 | |
| GB | 2 178 442 A | 2/1987 | |
| WO | WO 82/03532 | 10/1982 | |
| WO | WO 97/47721 | 12/1997 | |
| WO | WO 99/55813 | 11/1999 | |
| WO | WO 01/16264 | 3/2001 | |
| WO | WO 01/43567 A1 | 6/2001 | |
| WO | WO 01/94520 A2 | 12/2001 | |
| WO | WO 02/40792 A1 | 5/2002 | |
| WO | WO2005046632 * | 5/2005 | ............... A61K 7/46 |

OTHER PUBLICATIONS

Graffeo et al. (Clinical Chemistry vol. 22 No. 2 pp. 184-187 1976).*
Sato et al Journal of Health Science vol. 47 No. 5 pp. 483 to 490.*
Carnes et al. Journal of Laboratory and Clinical Medicine 1938 vol. 23 pp. 459-463.*
European Search Report for corresponding European Patent Application 06 300 859, mailed on Feb. 22, 2007.

* cited by examiner

*Primary Examiner* — Patrick Ryan
*Assistant Examiner* — Aaron Greso
(74) *Attorney, Agent, or Firm* — Merchant & Gould P.C.

(57) ABSTRACT

The use of fragrance compositions comprising fragrance compounds selected among: aldehydes, α,β-unsaturated aldehydes, alcohols, ketones, and mixtures thereof in any home and personal care product, each fragrance compound being able to restrict the formation of indole to less than 0.01 ppm (wt/wt) after 24 hours incubation at room temperature in an airtight sealed vessel of suitable fresh human urine containing 0.28% by weight of each fragrance compound in order to prevent the development of indole based malodours from faecal and urine based soils.

22 Claims, 1 Drawing Sheet

USE OF FRAGRANCE COMPOSITIONS FOR THE PREVENTION OF THE DEVELOPMENT OF INDOLE BASE MALODOURS FROM FECAL AND URINE BASED SOILS

CROSS-REFERENCE TO RELATED APPLICATIONS

This application is a Continuation of U.S. Ser. No. 11/499,226, filed on Aug. 4, 2006 and which application is incorporated herein by reference. A claim of priority, to the extent appropriate is made.

TECHNICAL FIELD OF INVENTION

The invention relates to fragrances and fragrance ingredients which can be used in a variety of products to prevent the development of malodours derived from the action of micro-organisms on excreted matter such as urine or faeces. The present invention aims to prevent the creation of malodorous compounds based on indole and related compounds.

BACKGROUND OF THE INVENTION

Perfumes are used in many applications to mask malodours. A particularly important category of malodours are, for example, those resulting from substances transpired by or excreted by humans in particular perspiration, urine, faeces or menstrual fluid, and odours caused by animal urine or faeces, especially those of domestic pets.

Malodours are usually caused by particularly odorous substances such as sulphur compounds e.g. hydrogen sulphide, and low molecular weight thiols and thioethers, nitrogen containing compounds such as ammonia and amines including heterocyclic compounds such as pyrazines and indoles, oxygen containing compounds such as fatty acids and steroids. These malodorous compounds are often created by the action of micro-organisms on excreted material or during the digestion of food or drink. As natural products the malodours are themselves complex mixtures, not only of several compounds within each of the above categories but also including members of all the categories to different degrees depending on the source of the odour. Consequently preventing, countering, reducing or destroying malodour is not straightforward.

Various methods have been developed to counter or reduce malodour beyond odour masking with strong fragrance. Activated carbon and zeolites have been used as absorbents for malodours but these are not suited for incorporation into many products. Antimicrobial agents such as zinc compounds and Triclosan (2',4',4'-trichloro-2-hydroxy-diphenyl ether) are used to kill microorganisms involved in producing malodours, but many are non-specific and can lead to imbalances in the natural microflora.

U.S. Pat. Nos. 4,304,679; 4,322,308; 4,278,658 and 4,134,838 all describe fragrances which exhibit a deodorant action when applied to human skin or when included in a laundry product. These are believed to work by any or all of a variety of mechanisms: reducing the vapour pressure of malodorous compounds, inhibiting the enzymes which generate the malodours and combining with the malodour to modify the perceived odour note.

U.S. Pat. No. 4,719,105 describes the use of cyclomethanols and esters as low odour materials which can be used to mask malodours without having unduly strong fragrances themselves.

US patent application 2004/0147416 describes the use of cyclodextrins to trap malodorous molecules.

Malodours tend to become stronger over time as the population of micro-organisms grows and malodour production increases. Herein lies a major disadvantage of using perfumes to mask malodour. While a perfume can mask a malodour just after application, over time the intensity of the fragrance decreases, whereas the malodour will in all probability increase in intensity from the growing micro-organism colonies. The same argument can be applied equally well to counteractants which work by reacting with malodorous molecules, in time they will be overwhelmed by the malodours. Their effect is to delay or reduce the intensity of the malodour and as such this may be sufficient for some commercial applications.

A different approach is to inhibit specific biological pathways. Compounds which act more specifically include saturated $C_3$-$C_{10}$ dioic acids which inhibit a sweat decomposing esterase as described in DE patent application 4,343,265.

U.S. Pat. No. 6,183,731 describes the use of agents which are inhibitors of 5α-reductase, such as octadecendioic acid as a preventative agent for body malodour.

U.S. Pat. No. 5,395,555 teaches an aqueous cleaning composition for carpets, rugs, and textiles, particularly useful in reducing malodour of urine stains containing selected metal sequestrants which is thought to deny heavy metals essential to the micro-organisms' development.

However as mentioned earlier malodours are complex and such approaches may not counter all the components of the malodour, so it is more likely that they modify the nature of the odour which again may be a worthwhile benefit but is only a partial solution to the problem.

Aldehydes are sometimes cited as malodour counteractants. U.S. Pat. No. 4,906,454 describes piroctone acid and a perfume with a high concentration of aldehydes and/or ketones for use in deodorants in preventing body malodours. U.S. Pat. No. 6,177,070 describes a deodorant product containing at least two different aldehydes present in the form of addition compounds such as acetals and hemi-acetals and an unsaturated compound. This is quite different from the aldehydes in the present invention which are not present as addition compounds but comprise part of the fragrance added directly to the product.

US patent application 2005/0124512 describes the use of fabric safe aldehydes (i.e. non discolouring) as components of air or fabric freshening spray products which react with malodorous components in air. There is nothing in this patent which teaches that the aldehydes might inhibit odour formation especially that they might do so in a non reactive way which leaves the fragrance unimpaired.

U.S. Pat. No. 5,676,163 describes two classes of aldehydes which act additively or synergistically to reduce the malodour of tobacco smoke. Again the patent only teaches that aldehydes react with some malodorous molecules and there is no evidence for the prevention of biologically generated malodours.

US patent applications 2005/1087123 and 2005/0187124 describe compositions to be incorporated into solid and liquid carpet cleaner and de-odourising products to remove malodours from carpets. In US patent application 2005/0187123 aldehydes are optional components of the mixture and there is no teaching beyond their having an odour reaction and masking effect. However in co-filed US patent application 2005/187124 aldehydes are described as enzyme inhibitors whilst aldehydes and ketones are described as odour reactants. No evidence is given as to which enzymes are inhibited or which malodorous compounds reduced or prevented and only benzaldehyde would be considered as a fragrance aldehyde among the group of aldehydes cited and the efficacy of benzaldehyde is not demonstrated in the examples.

US patent application 2002/0010447 describes two categories of aldehydes for malodour reduction in fibrous absorbents for bodily fluids. The categories of aldehydes which are claimed to work synergistically are aliphatic aldehydes and aldehydes which have an sp2 hybridised carbon in the alpha position to the aldehyde carbon. Again there is nothing in the text to suggest that the aldehydes have any inhibitory effect beyond chemical reaction or vapour pressure reduction.

US patent application 2003/0044309 describes mixtures of two types of aldehydes for malodour counteraction in carpet cleaners but all of the examples described intimate mixing of the test formulation with the malodour source allowing for chemical reaction. Nowhere does the document suggest that indole based malodours might be prevented.

From all of the prior art references and examples, aldehydes with the specific exception of formaldehyde are predominantly considered to work by chemical reaction with a pre-existing odorant rather than the specific prevention of indole based malodours. Formaldehyde is well known as an antimicrobial agent which is frequently incorporated into formulations directly or in the form of any of several derivatives which release formaldehyde slowly.

Thus while it is apparent from the prior art that there are many methods which attempt to prevent malodour, none are completely satisfactory. The present invention describes a simple and inexpensive way to prevent the development of some of the components of urinous or fecal malodours via specific ingredient selection within the fragrance incorporated into a wide range of household and personal care products.

SUMMARY OF THE INVENTION

The present invention relates to the use of fragrance compositions, said fragrance compositions comprising fragrance compounds selected amongst aldehydes, $\alpha,\beta$-unsaturated aldehydes, alcohols, ketones and mixtures thereof in any home or personal care product, each fragrance compound being able to restrict the formation of indole to less than 0.01 ppm (wt/wt) after 24 hours incubation at room temperature in an airtight sealed vessel of suitable fresh human urine containing 0.28% by weight of each fragrance compound in order to prevent the development of indole based malodours from faecal and urine based soils.

In the present specification the "home or personal care products" designate all the products usually used in the care of the home and body, particularly:
a) rim block products, cistern block or liquid rim block products,
b) hard surface liquids, gel or paste household cleaners,
c) soft furnishing cleaners or refreshers particularly liquid sprays,
d) air fresheners,
e) animal litters,
f) personal care fibrous liquid absorptive devices such as sanitary towels, babies nappies or incontinence products, A particularly preferred form of the invention relates to the use of fragrance compositions comprising of fragrance compounds selected among: aldehydes, $\alpha,\beta$-unsaturated aldehydes, alcohols and ketones as defined above, but without themselves decreasing in concentration by no more than 60% by weight, preferably no more than 30% by weight after 24 hours incubation at room temperature in an airtight sealed vessel of suitable fresh human urine containing 0.28% by weight of each fragrance compound for use in any home or personal care product in order to prevent the development of indole based malodours from faecal and urine based soils.

A further preferred form of the invention relates to the use of fragrance compounds selected among: aldehydes, $\alpha,\beta$-unsaturated aldehydes and allylic alcohols which satisfy the indole inhibition test as defined above for use in any home or personal care product in order to prevent the development of indole based malodours from faecal and urine based soils.

DETAILED DESCRIPTION OF THE INVENTION

The present invention relates to the use of fragrance compositions comprising fragrance compounds, preferably containing 2.5% to 100%, more preferably containing 10% to 100%, even more preferred is 20% to 100% and especially preferred is 40% to 100% by weight of fragrance compounds which are selected amongst aldehydes, $\alpha,\beta$-unsaturated aldehydes, alcohols or ketones and mixtures thereof, each fragrance compound being able to restrict the formation of indole to less than 0.01 ppm (wt/wt) after 24 hours incubation at room temperature in an airtight sealed vessel of suitable fresh human urine containing 0.28% by weight of each of the said fragrance compounds in order to prevent the development of indole based malodours from faecal and urine based soils.

A particularly preferred form of the invention relates to the use of fragrance compositions comprising of fragrance compounds, preferably containing 2.5% to 100%, more preferably containing 10% to 100%, even more preferred is 20% to 100% and especially preferred is 40% to 100% of which are selected amongst: aldehydes, $\alpha,\beta$-unsaturated aldehydes, alcohols and ketones and mixtures thereof, as defined above, without themselves decreasing in concentration by no more than 60% by weight, preferably no more than 30% by weight after 24 hours incubation at room temperature in an airtight sealed vessel in the above defined conditions, for use in home and personal care products in order to prevent the development of indole based malodours from faecal and urine based soils.

The effective compounds of the invention are fragrance materials which are aldehydes, $\alpha,\beta$-unsaturated aldehydes, alcohols or ketones which pass the indole inhibition test, i.e. which are able to restrict the formation of indole to less than 0.01 ppm (wt/wt) of indole compounds after 24 hours incubation at room temperature in an airtight sealed vessel in the above defined conditions.

Suitable Fresh Human Urine

Urine is a variable material and it has been found that not all batches of urine are suitable for conducting the indole inhibition test. Hence it is essential that a blank sample of fresh human urine is tested at the same time as the samples containing the candidate fragrance compounds and only if this blank urine samples complies with certain criteria can the result of the fragrance compound test be accepted as valid. In order to ensure that the fresh human urine is suitable, the urine should have less than 0.01 ppm (wt/wt) indole at the start of the experiment and after 24 hours storage at room temperature in an airtight sealed vessel it should contain between 0.25 ppm (wt/wt) and 1.25 ppm (wt/wt) indole as determined by the test method described below. Only if the urine blank conforms with both criteria can the results for any fragrance compound tested be considered valid. If the urine blank does not meet both criteria then the results for any fragrance compound tested must be discarded and a new batch of urine tested.

Without wishing to be bound by theories, it seems that the compounds of the invention interfere with the biological process of tryptophan metabolism rather than as a reagent. That many of the effective compounds remain little changed whilst being highly effective is an important benefit for the present invention. If compounds react with malodours then the fragrance note must change which presumably diminishes the quality of odour carefully created by the perfumer.

In a preferred aspect of the invention the change in aldehyde, alcohol or ketone concentrations is less than 60% preferably less than 30%, so maintaining the original fragrance note.

For those aldehydes, alcohols and ketones which decrease over time it is possible that they may react with ammonia or other amine species but this is not desirable nor the major aspect of the invention. However, due to the complexity of different product formulations, fragrances within those formulations, and malodours, any or all of which may affect the availability of active agents for reaction, as well as the inherent reactivity of individual compounds we do not wish to speculate further on this point.

Perfume Composition

In the context of this specification a "fragrance composition", which is also named "perfume composition" is an essential part of the invention. The term "perfume composition" means any mixture, i.e. more than one chemical species, of odiferous materials including materials which act as malodor counteractants. A wide variety of chemicals are known for perfumery use, including materials possessing the required chemical functional groups of the invention aldehydes, $\alpha,\beta$-unsaturated aldehydes, alcohols, including allylic alcohols and ketones but also including alkenes, esters, ethers, nitriles, amines, oximes, acetals, ketals, thiols, acetals etc. Without wishing to be limited, the perfume compounds will preferably have molecular weights of less than 325 atomic mass units, preferably less than 300 mass units and more preferably less than 275 mass units to ensure sufficient volatility to be perceivable. Furthermore the perfume compounds will have molecular weights greater than 100 mass units, preferably greater than 120 mass units as lower masses may be too volatile to inhibit malodour generation for any length of time. Furthermore ingredients of the fragrance compositions will not contain strongly ionizing functional groups such as sulphonates, sulphates, or quaternary ammonium ions which prevent volatilisation.

Naturally occurring plant and animal oils and exudates comprising complex mixtures of various chemical components are also known for use as perfumes, and such materials can be used herein. Perfume compositions of the present invention can be relatively simple in their composition with a minimum of two perfume or fragrance ingredients or can comprise highly complex mixtures of natural and synthetic chemical components, chosen to provide any desired odour. Perfume ingredients are described more fully in S. Arctander, Perfume Flavors and Chemicals. Vols. I and II, Montclair, N.J., and the Merck Index, 8th Edition, Merck & Co., Inc. Rahway, N.J., both are incorporated herein by reference.

Not all fragrance compounds possessing the aldehyde, alcohol and ketone groups are effective in preventing indole derived malodours. The indole inhibition test is therefore described as a way of determining which compounds are effective.

The selection of the appropriate fragrance compounds useful in the present invention may be easily made by the person skilled in the art by detecting the indole inhibition effect provided by those fragrance compounds by measuring formation of indole after 24 hours incubation at room temperature in an airtight sealed vessel of fresh suitable human urine containing 0.28% by weight of each fragrance compound and comparing the indole formation with a control stored in the same conditions. The formation of indole may be determined by any analysis techniques well known by the person skilled in the art, for example by detecting the characteristic ions of indole under standard GC-MS conditions.

The aldehydes, $\alpha,\beta$-unsaturated aldehydes, alcohols, ketones, or mixtures thereof which are useful for the invention purposes are those which restrict the formation to less than 0.01 ppm (wt/wt) of indole under the above conditions.

Room temperature is defined as being within 18° C. to 22° C.

Indole Inhibition Test

Advantageously, the appropriate fragrance compounds may be selected by using the following preferred indole inhibition test which comprises the following steps:

A) 0.02 g of fragrance and 0.02 g of Tergitol 15-s-12 was added to 7 g of fresh human urine in a 20 ml Headspace vial sealed with a PTFE faced septum and well mixed for 10 minutes using a magnetic stirrer. For a blank to test the suitability of a batch of fresh human urine, 7 g of human urine was used with 0.02 g of demineralised water and 0.02 g of Tergitol 15-s-12. If a control was required, to test the efficacy of product base for example, the control contained 7 g of human urine to which was added 0.02 g of fragrance, minus the active agents and 0.02 g of Tergitol 15-s-12.

B) The vials are placed in an autosampler tray at room temperature.

C) At different times the headspace in the vials is sampled for 5 minutes at 35° C. by an SPME fibre (PDMS fibre ex Supelco) after 10 minutes at 35° C. (incubation time).

D) The SPME fibre is desorbed 1 minute at 265° C. from a CTC Combipal autosampler and injected in splitless mode onto an Agilent GC-MS 5973N with a HP-INNOWAX column (30 m×0.25×0.25). (Oven conditions: 50° C. during 2 min-to 250° C. at 10° C./min-250° C. during 5 minutes).

E) Under the above GC-MS conditions, indole has a retention time of 19.14 minutes, and can be recognised by its characteristic ions (m/z 117, m/z 89 and m/z 90).

F) In the range of values determined in this work, the area of the indole peak (117) is linearly related to the actual concentration in the vial, and was used without further correction to establish the concentration of indole in "Active" and "Blank" and if present any "Control" fragrances.

G) The material is deemed to be active if the indole concentration in the test sample is below 0.01 ppm (wt/wt) after 24 hours incubation at room temperature and the indole in the blank samples is between 0.25 ppm (wt/wt) and 1.25 ppm (wt/wt) indole after 24 hours storage at room temperature.

H) The change in the active ingredient concentration is determined by comparing measurements at the start of the experiment and after 24 hours using appropriate characteristic ions.

Figure 1:
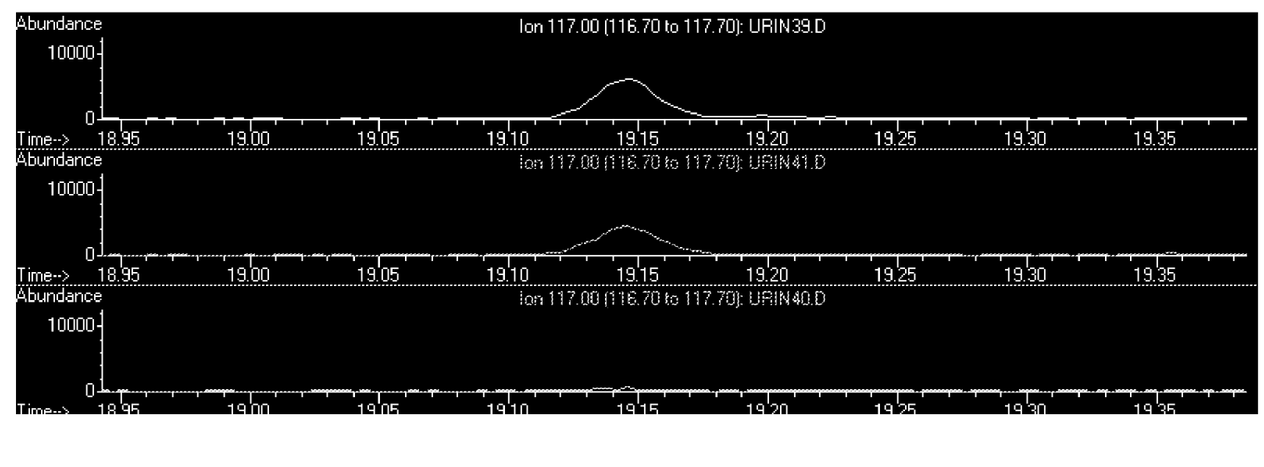
FIG. 1 shows, GC MS chromatograph for indole showing the mass abundance for m/e 117 characteristic of indole at a retention time of 19.14 minutes also characteristic of indole under the GC conditions employed, for the blank (file URIN39.D) and the active fragrance composition of example 2 (file URIN40.D)

FIG. 1 compares the indole peaks for a blank, control sample and active fragrance composition of example 2 in a liquid rim block.

A calibration line has been derived to quantify indole by making up a series of standard solutions containing accurately measured amounts of indole in fresh human urine and Tergitol 15-s-12 which were measured according to the method described. This calibration is essentially linear to 0.01 ppm of indole and below that level the indole cannot be quantified. Tergitol 15-s-12 is a trade name of the Dow Chemical company for a commercial grade of a secondary alcohol ethoxylate surfactant. It is also available from Sigma Aldrich. Tergitol 15-s-12 and identical products from other suppliers have the Chemical abstracts number CAS 68131-40-8. Tergitol 15-s-12 acts as a solubilising agent for fragrance ingredients which might not be directly soluble in urine at that concentration.

The efficacy of fragrances in products may be detected by using the above defined protocol starting from an aliquot of fragranced product containing 0.02 g of fragrance compound was added to 7 g of fresh suitable human urine in a 20 ml headspace vial sealed with a PTFE faced septum and well mixed for 10 minutes using a magnetic stirrer. For a blank, to assess the suitability of the urine, 0.02 g of demineralised water and 0.02 g of Tergitol 15-s-12 was added to 7 g of an identical sample of human urine and for any control, to assess whether other parts of the formulation could inhibit urine formation, the same weight of product containing 0.02 g of fragrance, minus any known active ingredients was added to another 7 g of human urine taken from the same batch as is used for the sample and blank.

There is a benefit to selecting aldehydes, α,β-unsaturated aldehydes, alcohols and ketones which do not change concentration during the course of the indole inhibition test, since the fragrance note will not be adversely affected by depletion of the effective fragrance compounds. This can be determined by measuring the fragrance concentration in the sample containing the test cocktail at the start and end of the indole inhibition test as described in step I of the test. If the difference between the measurements is less than 60% preferably less than 30% then the material is considered as not to have changed sufficiently to alter the fragrance note and to be particularly preferred.

The present invention also relates to the use of a fragrance compound selected among acetophenone, aldehyde C-11, aldehyde C-10, benzaldehyde, benzophenone, cinnamic aldehyde, citronellal, citral, heliobouquet, trans 2-hexenal, trans 2-hexenol, perilla aldehyde, perilla alcohol, and veltol Plus or their mixtures, as indole inhibitors.

The invention also relates to the use of a fragrance compound selected among: acetophenone, aldehyde C-11, aldehyde C-10, benzaldehyde, benzophenone, cinnamic aldehyde, citronellal, citral, heliobouquet, trans 2-hexenal, trans 2-hexenol, perilla aldehyde, perilla alcohol, and veltol Plus or their mixtures, for the preparation of a fragrance composition intended to prevent the development of indole based malodours from faecal and urine based soils.

Optional Ingredients

It is often desirable to combine methods to counter or prevent the development of malodours. Thus the following are optional ingredients which may be used advantageously in some of the products to reduce malodour still further. Because of the diverse range of products from which the invention may be delivered not all of the optional ingredients would be suitable for all of the potential product applications but those skilled in the formulation of these products will recognise which ingredients are suitable and which are not.

Sequestrants

Examples of sequestrants which have antimicrobial and enzyme inhibitory effects in their own right or may potentiate the efficacy of conventional biocides include aminocarboxylates such as ethylene diamine tetraacetic acid (EDTA), diethylene triaminepentaacetic acid, amino phosphonates, such as hydroxyethane-dimethylene-phosphonic acid, ethylene diamine tetra(methylene phosphonic) acid, diethylene triamine penta(methyl phosphonic) acid, and their salts either used individually or in admixture. Especially preferred are the biodegradable sequestrants, exemplified by, but not limited to, S,S-ethylene diamine disuccinic acid, and its salts or glutamic acid N,N-diacetic acid tetra sodium salts (Dissolvine GL-38 ex Akzo Nobel) and combinations thereof. Because of the diversity of product forms and the possibility that some products could be diluted in water which may have a significant calcium and magnesium content, "hard water", the sequestrant can be included at any of a wide range of concentrations in formulations from 0.01-0.5%.

Antimicrobial Agents

Broad spectrum antimicrobial agents which might advantageously be used in conjunction with the present invention are: cationic agents such as quaternium 15, benzalkonium chloride, cetrimonium chloride, myristalkonium chloride, cetylpyridinium chloride, lauryl pyridinium chloride and the like. Non limiting examples of acids and their associated anions which have antimicrobial properties include sorbic acid, benzoic acid, and dehydroacetic acid. Other antimicrobials include benzyl alcohol, phenylethyl alcohol, DMDM-hydantoin, imidazolidinylurea, 2 bromo-2-nitropropane-1,3-diol and 4,4-dimethyloxazolidine. Phenolic antimicrobials which might be used include chloroxylenol, salicylic acid, and isothiazoline derivatives sold under the Kathon (Lonza) and Proxel and Proxemal (Astra Zeneca) trade names.

Malodour Absorbers

Malodour absorbers include zinc ricinoleate sold as Tego Deo by Degussa and cyclodextrins as described in U.S. Pat. Nos. 5,942,217; 5,955,093 and 6,033,679. Other absorbents which may be used in pet litter trays and might absorb malodours include clays or zeolites.

Products for Application of the Invention

Lavatory Solid Rim Blocks and Cistern Blocks

One embodiment of the present invention relates to lavatory blocks including those which are intended, in use, to be located under the rim of a lavatory bowl or urinal such that, during a flushing cycle, water from the cistern flows over the block thereby dissolving a portion of the block. Such blocks are generally known in the art as 'rim blocks' and will be referred to as such or simply as 'blocks' herein. The invention also relates to so-called cistern blocks which are placed in the cistern and dissolve slowly in the water contained therein. It will be appreciated that the solubility characteristics of these two products are quite different, since one is constantly under water while the other has intermittent short term contact with water. However they both contain a surfactant, a filler, a fragrance which may contain ingredients of the present invention and optionally bleaching agents, germicides and anti-limescale agents. Typical formulations are taught in international patent applications WO97/7721, WO82/03532, European patent application 0 462 643, UK patent application 2 178 442 and U.S. Pat. No. 4,874,536 all of which are incorporated herein by reference.

Liquid Rim Blocks

Another embodiment of the fragrances of this invention relates to lavatory cleaners known as liquid rim blocks. Liquid rim blocks are devices that dispense liquid compositions directly into a lavatory bowl from under the rim of said bowl. Such rim blocks are usually attached by various means, such as hooks and the like, to the rim of the lavatory bowl. Every time a toilet equipped with a rim block is flushed, an amount of composition is dispensed into the lavatory bowl. Examples of liquid rim blocks are given in international application WO02/40792 which teaches a liquid rim-block device having a suspension means and at least two compartments for active substances. International application WO 02/04951 teaches a liquid rim block, a lavatory cleaning system comprising a dispenser for dispensing a liquid composition from under the rim of a lavatory bowl, wherein the composition has a viscosity of greater than 2500 mPa·s. Other similar systems are described in European patent application 0 775 741 and International application WO01/94520 all of which are incorporated herein by reference.

Liquid Hard Surface Cleaner Formulation

A further embodiment of the invention relates to hard surface cleaner formulations also known as all purpose cleaners or general purpose cleaners. They are a broad category of products including isotropic liquids, thickened liquids with or without abrasive or as a mousse. They can be used directly from the bottle or after dilution in water. Various delivery methods have been devised for the convenience of the user, some are sprayed onto surfaces from trigger spray bottles, alternatively they can be poured directly onto surfaces and removed for instance when a lavatory is flushed. They may contain additional ingredients such as acids for limescale removal, biocides for hygiene, or bleaches. Consequently there are a broad range of formulations within this category. Table 1 below summarises the main formulation ingredients and levels (this is taken from Surfactant Science Series Vol 67 Liquid Detergents chapter on Specialty Liquid Household Surface Cleaners p 479 table 4.) In all cases, except when oxidizing bleaches (eg sodium hypochlorite or hydrogen peroxide) are incorporated into the formulation, fragrances incorporating this invention may be used as the fragrance within the product.

TABLE 1

Formulation Range For Household Cleaners

| Ingredient | Example | Amount wt % |
|---|---|---|
| Anionic surfactant | Alkylbenzene sulphonate, as supplied by Shell as Dobs 055, alkane sulphonate eg Hostaspur SAS60 | 0-35 |
| Nonionic surfactant | Ethoxylated alcohol eg Neodol 9-11 6EO, mixed ethoxy/propoxy alcohol such as the pluronic series from BASF, amine oxide, alkanolamides and betaines | 1-35 |
| Hydrotropes | Sodium cumene sulphonate or xylene sulphonate | 0-10 |
| Builder/sequestrant | Citrates, EDTA salts, phosphonate salts, lactic acid and polyacrylates | 0-10 |
| Solvent | Lower alcohols, glycol ethers, benzyl alcohol, or hydrocarbons eg limonene | 0.5-50 |
| Disinfectant | Hypochlorite bleach, pine oil, lower alcohols, quaternary ammonium salts | 0-15 |
| Perfume, colour, thickening polymer, sequestrant, preservatives | | 0.1-3 |
| Water | | To 100 |

Pet Litter

The increase in animal pet population has led to an increasing use of animal litter materials. There are numerous animal litter products available commercially and taught by prior art. They are usually based on inexpensive materials such as abundant natural minerals e.g. sand, granulated clays or zeolite, or recycled waste cellulosic materials such as woodchips, sawdust, shredded paper, pelleted or shredded recycled cloth, ground wood bark, alfalfa or other vegetable matter such as ground corn husk. In order to improve the performance of animal litters additional materials are added to improve absorbancy, to clump the particles, to ease disposal and odour treatment agents. U.S. Pat. No. 4,437,429 teaches using zeolite to control odours in clay based litter. U.S. Pat. No. 3,789,717 combines bentonite clay with alfalfa which supplies chlorophyll as a deodorizer. Fragrances of the present invention can either be incorporated into the pet litter during manufacture or added later in use.

Carpet Cleaners

Carpet cleaners come in several forms: powders, liquids, foams and spray spot treatments. Many of these products have to be used in conjunction with a specific cleaning machine especially if large areas are to be treated. However a desirable attribute of cleaning a carpet is to leave a pleasant smell so the products generally contain a fragrance and fragrances of the present invention are both suitable and desirable for application in carpet cleaning products.

Air Freshener, Textile and Soft Furnishing Deodourising Sprays

Products for reducing or masking malodours in the air or on textiles and soft furnishings are known, such as Glade by SC Johnson and Febreze from Proctor and Gamble. These products are designed to be sprayed into the air or onto surfaces. They can be dispensed either from aerosols with a volatile propellant gas or using a trigger spray which does not require propellant gas. US patent application 2005/0124512 teaches a cyclodextrin containing product in which non fabric discolouring aldehydes are incorporated to react with amines in the air. Nowhere does the patent teach that aldehydes might inhibit malodour formation without reacting themselves. US patent application 2003/0044309 teaches an emulsion composition containing a selection of fragrance aldehydes which counter pre-existing malodours when in direct contact with fabrics which again teaches reactive chemistry rather than prevention of indole based malodour development. Fragrances incorporating indole inhibiting materials can also be used advantageously in these products.

Room Air Fresheners

Products for freshening or fragrancing general ambient air countering malodours or repelling insects devices include devices which have no power source and work by diffusion or by electrical heating a wick in contact with a liquid reservoir so that the rate of fragrance can be controlled. Such devices can be mains powered so called plug-in fresheners as described in U.S. Pat. No. 6,917,754 or battery powered so portable or for use in a motor vehicle. Optionally the device may use an atomizing spray to disperse the fragrance or contain an electrically powered fan. Fragrance compositions of the present invention can be dispersed by these freshener devices and settle on surfaces to prevent malodour developing.

Fibrous Articles Intended for the Absorption of Bodily Fluids

Considerable success has been achieved in the design of products intended to absorb and retain human and animal waste materials. The construction of articles such as disposable diapers and training pants, sanitary napkins and tampons and incontinence products for example has become sophisticated with the addition of elastics, barrier layers superabsorbing polymers and the like to retain more waste and prevent leakage. Reference may be made to U.S. Pat. Nos. 4,846,823; 5,932,495 or 4,335,722 which are incorporated herein by reference for descriptions of the technology. The control of odour remains a challenge that is exacerbated by the technical improvements mentioned above, which has led to larger quantities of waste being contained in products designed to require changing less frequently.

Attempts to prevent such odours from forming or to absorb those formed have often involved antimicrobial treatments. The use of additives such as activated carbon, zeolites, metals such as copper, metal oxides, alumina hydrate, minerals such as holmite, laconite, kaolin and modifications of molecular sieves have been suggested as well as the use of acid/base interactions to neutralize the various odor forming components. U.S. Pat. No. 6,031,147 teaches the use of surfactants to suppress the odour in disposable absorbent products. US patent application 2002/0010447 also teaches several of the above and also the use of a mixture of two types of aldehydes but it does not teach that aldehydes prevent the development of malodours associated with indolic compounds, nor that the aldehydes are unchanged by the interaction. In spite of these efforts, there remains a need to control odours better.

Example 1

Identification of Active Fragrance Compounds

A sample of fresh human urine is divided into equal portions and a fragrance containing one or more of the effective materials was added as described in the Indole Inhibition Test. Control samples were prepared in which inactive compounds were substituted and a third unfragranced blank was also prepared to determine the suitability of the urine. The samples were stored and after 24 hours the indole content and fragrance active content is measured by gas chromatography with mass spectrometric (GCMS) detection. Those formulations containing active ingredients prevented the formation of indole while both the unfragranced and the alcohol containing control samples had much greater quantities of indole present. Also for the active compounds a GCMS measurement indicated the extent to which the compound was itself consumed as part of the process. In table 2 the decrease in fragrance components has been classified into 3 categories and the letter Y indicates the appropriate category for the compounds which have been measured. The absence of a letter Y in any category means that the decrease has not been measured for that compound.

TABLE 2

Examples of effective materials

| Active Compounds/CAS Nos | Decrease in Fragrance Compounds after 24 hours (%) | | |
|---|---|---|---|
| | 0-30% | 0-60% | >60% |
| Acetophenone 98-86-2 | | | |
| Benzaldehyde 100-52-7 | Y | | |
| Benzophenone 119-61-9 | | | |
| Cinnamic aldehyde 104-55-2 | Y | | |
| Citronellal 5949-05-3 | | | |
| Trans 2 hexenal 6728-26-3 | | Y | |
| Trans 2 hexenol 928-95-0 | | | |
| Aldehyde C11 112-44-7 | | | Y |
| Citral 5392-40-5 | Y | | |
| Aldehyde C-10 112-31-2 | | | |
| Perilla aldehyde 2111-75-3 | Y | | |
| Perilla alcohol 536-59-4 | | | |
| Veltol Plus 4940-11-8 | | | Y |
| Heliobouquet 1205-17-0 | | | |

Y = Yes

The following compounds were found to be ineffective at reducing indole levels in urine over 24 hours.

Inactive Compounds/CAS Nos:
Benzyl alcohol 100-51-6
Phenyl ethyl alcohol 60-12-8
Cinnamic alcohol 104-54-1
Citronellol 106-22-9
Alcohol C10 112-30-1
Hexyl cinnamic aldehyde 101-86-0
Amyl cinnamic alcohol 101-85-9
Kovanol 31906-04-4
Anisic Alcohol 105-13-5
Dimethyl Octenone 2550-11-0
Dimethyl Octanol 106-21-8
α Damascone 24720-09-0
Phenylacetaldehyde 122-78-1
Lilial 80-54-6
Laurinal 107-75-5
Geraniol 106-24-1
Nerol 106-25-2
B Ionone 14901-07-6
Cyclamen aldehyde 103-95-7
Myrac aldehyde 37677-14-8
Vanillin 121-33-5
Ethyl vanillin 121-32-4
Canthoxal 5462-06-6
Cuminic ald 122-03-2
Phenoxanol 55066-48-3
Triplal 68039-49-6

Example 2

Performance from a Liquid Rim Block

The active composition of Table 3 (example 2) was mixed into a liquid rim block formulation having the composition of example 6 of which 0.25 g was added to 7.0 g of a fresh suitable human urine sample to give 0.02 g of active fragrance as described in part B of the indole inhibition test. After 24 hours the indole content was measured and the result shown as file URIN40.D in FIG. 1. Comparative example A control was mixed with the same liquid rim block formulation and gave the results in file URIN41.D in FIG. 1 while a blank sample containing 0.2 g of the liquid rim block formulation in urine gave file URIN39.D in FIG. 1. It can be seen the fragrance composition of the invention reduced indole concentration below 0.01 ppm (wt/wt). Note that the dosage of example 2 and comparative A in the liquid rim block represents about 30% of the normal total fragrance dose.

TABLE 3

Effectiveness in a Liquid Rim Block - Formulation of Active Components

| Example 2 | | Comparative Example A | |
|---|---|---|---|
| Compound | % | Compound | % |
| Benzaldehyde | 33.3 | Benzyl alcohol | 33.3 |
| Cinnamic Aldehyde | 33.3 | Cinnamic alcohol | 33.3 |
| Phenylacetaldehyde | 33.3 | Phenylethyl alcohol | 33.3 |

Example 3

Table 4 below demonstrates a fragrance composition according to the present invention containing 5% of active ingredient suitable for use in household products, along with a control fragrance comparative example B containing the corresponding inactive alcohols to the active aldehydes.

TABLE 4

Example of Effective and Ineffective Fragrances

| Example 3 | | Comparative Example B | |
|---|---|---|---|
| Compound | % | Compound | % |
| Benzaldehyde | 5 | Benzyl alcohol | 5 |
| Geraniol 98% | 20 | Geraniol 98% | 20 |
| Geranium oil Egypt nat | 2 | Geranium oil Egypt nat | 2 |
| Verdox | 5 | Verdox | 5 |
| Manzanate | 5 | Manzanate | 5 |
| Musk t-93 | 5 | Musk t-93 | 5 |
| Phenyl acetaldehyde | 10 | Phenyl ethyl alcohol | 10 |
| Phenyl ethyl alcohol | 42 | Phenyl ethyl alcohol | 42 |
| Phenylethylphenylacetate | 5 | Phenylethylphenylacetate | 5 |
| Rose oxide | 1 | Rose oxide | 1 |

Example 4

Table 5 demonstrates a fragrance composition according to the present invention containing 23% of active ingredients and suitable for use in household products, along with a control fragrance comparative example C containing the corresponding inactive alcohols to the active aldehydes

TABLE 5

Effective and Ineffective Fragrances

| Example 3 | | Comparative Example C | |
|---|---|---|---|
| Compound | % | compound | % |
| Adehyde C-10 FCC | 2 | Decanol | 2 |
| Aldehyde C8 | 1 | Octanol | 1 |
| Allyl caproate | 5 | Allyl caproate | 5 |
| Benzaldehyde | 10 | Benzyl alcohol | 10 |
| Citral | 10 | Citronellol | 10 |
| Citronellol | 10 | Citronellol | 10 |
| Citronellyl nitrile | 5 | Citronellyl Nitrile | 5 |
| Dihydromyrcenol | 15 | Dihydromyrcenol | 15 |
| Lemon oil | 5 | Lemon oil | 5 |
| Terpineol alpha | 35 | Terpineol alpha | 35 |
| Triplal | 2 | 2,4 dimethyl cyclohex-3-enyl methanol | 2 |

Example 5

Household Cleaner

Table 6 shows an example of a liquid household cleaner which can be used to deliver fragrances of the invention.

TABLE 6

Household Cleaner

| Ingredient | Purity | Wt % |
|---|---|---|
| Secondary alkane sulphonate Hostapur SAS 60 | 60 | 13.0 |
| Alcohol ethoxylate e.g. Neodol 91-6 EO | 100 | 2.0 |
| Lactic acid | 100 | 0.5 |
| Propylene glycol n butyl ether | | 0.5 |
| Perfume of composition as in example 3 | 100 | 0.35 |
| Preservative dye other minors | | q.s. |
| Water | 100 | To 100 |

Hostapur SAS 60 supplied by Clariant
Neodol 91-6 supplied by Shell Chemicals

Example 6

Liquid Rim Block

Table 7 shows an example of a liquid rim block which can be used to deliver fragrances of the invention

TABLE 7

Household Cleaner

| Ingredient | Wt % |
|---|---|
| Emulgin HF70 | 16.7 |
| 1,2 Propylene glycol | 4.0 |
| Perfume of composition as in example 3 | 8.0 |
| Kathon CG | 0.005 |
| Natrosol 250MR | 11.7 |
| Dyes and other minors | q.s. |
| Water | To 100 |

Emulgin HF70 supplied by Cognis
KathonCG supplied by Seppic
Natrosol 250MR supplied by Hercules Example 7

Table 8 shows an example of an acidic toilet bowl cleaner which can be used to deliver fragrances of the invention

TABLE 8

Toilet Bowl Cleaner

| Ingredient | Purity | Wt % |
|---|---|---|
| Secondary alkane sulphonate Hostapur SAS60 | 60 | 7.5 |
| Alcohol ethoxylate eg Neodol 91-6 EO | 100 | 3.0 |
| C12/18Amine oxide | 30 | 5.0 |
| Citric acid | 100 | 10 |
| Perfume of composition as in example 3 | 100 | 0.4 |
| Preservative dye other minors | | q.s. |
| water | 100 | To 100 |

Example 8

Concentrated Toilet Bowl Cleaner

Table 9 shows an example of a concentrated toilet bowl cleaner which can be used to deliver fragrances of the invention.

TABLE 9

Concentrated Toilet Bowl Cleaner

| Ingredient | Purity | Wt % |
|---|---|---|
| Secondary alkane sulphonate Hostapur SAS60 | 60 | 12.0 |
| Alcohol ethoxylate eg Neodol 91-7 EO | 100 | 9.0 |
| Citric Acid | 100 | 15 |
| Phosphoric acid | | 15.0 |
| Hordaphos CCMS | | 15.0 |
| Perfume of composition as in example 3 | 100 | 0.8 |
| Preservative dye other minors | | q.s. |
| Water | 100 | To 100 |

Hordaphos CCMS supplied by Clariant

Example 9

Acidic Abrasive Cleaner

Table 10 shows an example of an acidic abrasive liquid household cleaner which can be used to deliver fragrances of the invention

TABLE 10

| Acidic Abrasive Cleaner | | |
| --- | --- | --- |
| Ingredient | Purity | Wt % |
| Secondary alkane sulphonate Hostapur SAS60 | 60 | 5.3 |
| Alcohol ethoxylate eg Neodol 91-6 EO | 100 | 6.4 |
| Lactic acid | 100 | 3.3 |
| Water | 100 | 66.2 |
| Perfume of composition as in example 3 | 100 | 0.4 |
| Preservative dye other minors | | q.s. |
| Quartz powder* | 100 | 18.8 |
| Water | 100 | To 100 |

*eg Alsigra 25 from Alpha Calcit Fullstoff Gmbh

The invention claimed is:

1. A method of preventing the development of indole based malodour from faecal and urine based soils, the method comprising:
contacting the faecal or urine based soil with a home or personal care product comprising a fragrance composition, the fragrance composition comprising fragrance compounds selected from the group consisting of: aldehydes, α,β-unsaturated aldehydes, alcohols, ketones, and mixtures thereof;
wherein said fragrance compounds are effective to restrict the formation of indole to less than 0.01 ppm (wt/wt) and thereby prevent the development of said indole malodour, wherein the amount of indole is measured after 24 hours incubation at room temperature in an airtight sealed vessel of suitable fresh human urine containing 0.28% by weight of each fragrance compound, by comparison with a blank sample of suitable fresh human urine, the suitable fresh human urine having less than 0.01 ppm (wt/wt) indole at the start of the experiment and between 0.25 ppm (wt/wt) and 1.25 ppm (wt/wt) indole after 24 hours storage at room temperature in an airtight sealed vessel.

2. The method according to claim 1, wherein the fragrance composition comprises 2.5% to 100% by weight of fragrance compounds selected from the group consisting of aldehydes, α,β-unsaturated aldehydes, alcohols, ketones, and mixtures thereof.

3. The method according to claim 1, wherein the fragrance composition comprises 10% to 100% by weight of fragrance compounds selected from the group consisting of aldehydes, α,β-unsaturated aldehydes, alcohols, ketones, and mixtures thereof.

4. The method of claim 2, wherein the aldehydes, α,β-unsaturated aldehydes, alcohols, ketones, and mixtures thereof, decrease in concentration by no more than 60% by weight after 24 hours incubation at room temperature in an airtight sealed vessel of suitable fresh human urine containing 0.28% by weight of each fragrance compound.

5. The method of claim 2, wherein the fragrance compositions comprises 2.5% to 100% by weight of fragrance compounds selected from the group consisting of acetophenone, aldehyde C-11, aldehyde C-10, benzaldehyde, benzophenone, cinnamic aldehyde, citronellal, citral, heliobouquet (CAS 1205-17-0), trans 2-hexenal, trans 2-hexenol, perilla aldehyde, perilla alcohol, Veltol Plus (CAS no 4940-11-8) or their mixtures.

6. The method of claim 5, wherein the fragrance composition comprises 10% to 100% by weight of the fragrance compounds.

7. The method of claim 1, wherein the home or personal care product comprises a lavatory product.

8. The method of claim 1, wherein the home or personal care product comprises a fibrous absorbent article.

9. The method of claim 1, wherein the home or personal care product comprises a household cleaning product.

10. The method of claim 1, wherein the home or personal care product comprises animal litter.

11. The method of claim 1, wherein the home or personal care product comprises a trigger spray cleaner for soft furnishing.

12. The method of claim 1, wherein the home or personal care product comprises a carpet cleaning product.

13. The method of claim 2, wherein the fragrance composition comprises 20% to 100% by weight of fragrance compounds selected from the group consisting of aldehydes, α,β-unsaturated aldehydes, alcohols, ketones and mixtures thereof.

14. The method of claim 13, wherein the fragrance composition comprises 40% to 100% by weight of fragrance compounds selected from the group consisting of aldehydes, α,β-unsaturated aldehydes, alcohols, ketones and mixtures thereof.

15. The method of claim 1, wherein the fragrance compound comprises aldehydes, α,β-unsaturated aldehydes, or a mixture thereof.

16. The method of claim 2, wherein the aldehydes, α,β-unsaturated aldehydes, alcohols, ketones and mixtures thereof decrease in concentration by no more than 30% by weight after 24 hours incubation at room temperature in an airtight sealed vessel of suitable fresh human urine containing 0.28% by weight of each fragrance compound.

17. The method of claim 7, wherein the lavatory product comprises a rim block, a cistern block, or a liquid rim block.

18. The method of claim 8, wherein the fibrous absorbent article comprises a tampon, a sanitary towel, a baby's nappy, toddler pants, or an incontinence product.

19. The method of claim 8, wherein the fibrous absorbent article comprises a device intended for absorption of bodily excretions.

20. The method of claim 9, wherein the household cleaning product comprises a hard surface cleaner, a soft furnishing cleaner, or a room freshener.

21. A method of preventing the development of indole based malodor from faecal and urine based soils, the method comprising:
a) screening a fragrance compound selected from the group consisting of aldehydes, α,β-unsaturated aldehydes, alcohols, ketones, and mixtures thereof for its ability to restrict the formation of indole to less than 0.01 ppm (wt/wt), the screening comprising:
incubating suitable fresh human urine containing 0.28% by weight of the tested fragrance compound for 24 hours at room temperature in an airtight sealed vessel;
measuring the amount of indole by comparison with a blank sample of suitable fresh human urine;
the suitable fresh human urine having less than 0.01 ppm (wt/wt) indole at the start of the experiment and between 0.25 ppm (wt/wt) and 1.25 ppm (wt/wt) indole after 24 hours storage at room temperature in an airtight sealed vessel;

b) contacting a surface spoiled or to be spoiled by feces or urine with a home or personal care product comprising a fragrance composition, the fragrance composition comprising a fragrance compound identified in step a) to restrict the formation of indole to less than 0.01 ppm (wt/wt).

22. The method of claim 21 wherein the fragrance composition comprises 2.5% to 100% by weight of acetophenone, aldehyde C-11, aldehyde C-10, benzaldehyde, benzophenone, cinnamic aldehyde, citronellal, citral, heliobouquet (CAS 1205-17-0), trans 2-hexenal, trans 2-hexenol, perilla aldehyde, perilla alcohol, Veltol Plus (CAS no 4940-11-8), or mixtures thereof.

\* \* \* \* \*